United States Patent
Bui et al.

(10) Patent No.: US 7,530,557 B2
(45) Date of Patent: May 12, 2009

(54) MULTI-AXIS WORKPIECE CHUCK

(75) Inventors: Xuan S. Bui, Culver City, CA (US);
Michael Yang, Cerritos, CA (US); Gilles Lefebvre, Torrance, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 0 days.

(21) Appl. No.: 11/668,427

(22) Filed: Jan. 29, 2007

(65) Prior Publication Data

US 2007/0120304 A1 May 31, 2007

Related U.S. Application Data

(63) Continuation of application No. 10/763,710, filed on Jan. 22, 2004, now Pat. No. 7,168,694.

(51) Int. Cl.
*B23Q 3/18* (2006.01)
(52) U.S. Cl. .......................... 269/63; 269/60
(58) Field of Classification Search ............. 269/63, 269/60, 71–73; 29/559
See application file for complete search history.

(56) References Cited

U.S. PATENT DOCUMENTS

| | | | |
|---|---|---|---|
| 3,273,879 A | 9/1966 | Floren | |
| 3,552,733 A | 1/1971 | Pickett | |
| 3,962,937 A | 6/1976 | Miller | |
| 4,150,593 A | 4/1979 | Butler | |
| 4,492,356 A | 1/1985 | Taniguchi et al. | |
| 4,766,465 A | 8/1988 | Takahashi | |
| 5,156,019 A | 10/1992 | McCormick | |
| 5,355,439 A | 10/1994 | Bernstein et al. | |
| 5,746,855 A | 5/1998 | Bolles | |
| 5,930,461 A | 7/1999 | Bernstein et al. | |
| 6,199,623 B1 * | 3/2001 | Franks | 165/80.1 |
| 6,253,653 B1 | 7/2001 | Walter et al. | |
| 6,387,653 B1 | 5/2002 | Voneiff et al. | |
| 6,427,993 B1 | 8/2002 | Prochac | |
| 6,568,307 B1 | 5/2003 | Gunther et al. | |
| 6,634,268 B1 | 10/2003 | Guenther et al. | |

(Continued)

FOREIGN PATENT DOCUMENTS

GB 1190944 5/1970

*Primary Examiner*—Lee D Wilson
(74) *Attorney, Agent, or Firm*—Blakely Sokoloff Taylor & Zafman LLP

(57) ABSTRACT

A multi-axis chuck that rotates about at least two axes. Preferably, the axes are perpendicular. The multi-axis chuck includes a first portion, second portion, and third portion. Rear sides of the first portion and the second portion have a first mating portion that mates with a second mating portion provided on the second portion and the third portion, respectively. The mating portions enable the first portion and the second portion to be rotated about the axes. Preferably, the first portion rotates about a first axis independently of the second and third portions. Rotation of the second portion about a second axis preferably also rotates the first portion about the second axis. The multi-chuck is operatively connected to a motor, controller, and sensors. A user inputs a desired position into the controller that controls the motor. The motor rotates the multi-axis chuck to the desired position. The sensors are used to determine a position of the multi-axis chuck. The controller determines whether the position determined matches the desired position.

10 Claims, 3 Drawing Sheets

U.S. PATENT DOCUMENTS

| | | |
|---|---|---|
| 6,637,737 B1 * | 10/2003 | Beecherl et al. ............... 269/71 |
| 6,644,162 B1 | 11/2003 | Temple et al. |
| 6,874,773 B1 | 4/2005 | Newbould |
| 6,955,345 B2 * | 10/2005 | Kato ........................ 269/61 |
| 7,168,694 B2 * | 1/2007 | Bui et al. ...................... 269/63 |
| 7,287,388 B2 | 10/2007 | Dorenkamp et al. |
| 7,313,993 B2 | 1/2008 | Foerderer |
| 7,329,533 B2 | 2/2008 | Fredenburgh |
| 7,372,985 B2 | 5/2008 | So et al. |
| 7,374,907 B1 | 5/2008 | Voneiff et al. |
| 2002/0180133 A1 | 12/2002 | Oshima |
| 2003/0022271 A1 | 1/2003 | Voneiff et al. |
| 2003/0215936 A1 | 11/2003 | Kallioniemi et al. |
| 2005/0161873 A1 | 7/2005 | Bui |
| 2005/0226770 A1 | 10/2005 | Allen et al. |
| 2005/0235542 A1 | 10/2005 | Metzner et al. |
| 2006/0179992 A1 | 8/2006 | Kermani |
| 2007/0039435 A1 | 2/2007 | Kokubo |
| 2007/0120304 A1 * | 5/2007 | Bui et al. ...................... 269/63 |
| 2007/0180965 A1 | 8/2007 | Ito et al. |
| 2008/0072722 A1 | 3/2008 | Tanki et al. |
| 2008/0072723 A1 | 3/2008 | Nakajima et al. |
| 2008/0113440 A1 | 5/2008 | Gurney et al. |
| 2008/0202308 A1 | 8/2008 | Fujiwara et al. |

* cited by examiner

MULTI-AXIS WORKPIECE CHUCK

CROSS-REFERENCE TO RELATED APPLICATION

This application is a continuation of U.S. patent application Ser. No. 10/763,710, now U.S. Pat. No. 7,168,694, filed Jan. 22, 2004.

FIELD OF THE INVENTION

The invention generally relates to apparatus that holds a workpiece and orients it in different directions for cutting. More particularly, the invention concerns a chuck such as for holding a tissue specimen in a cutting device such as a microtome. The chuck can be rotated about at least two substantially perpendicular axes.

BACKGROUND OF THE INVENTION

Various forms of microtome chucks for retaining tissue workpieces for cutting are known. For example, known microtomes incorporate chucks that retain the tissue specimen block in a particular orientation for a cutting operation. In one example, the chuck moves relative to the blade while retaining the mounted tissue specimen in an otherwise fixed orientation.

One disadvantage of known microtome chucks is limitation on positioning the retained tissue specimen block. Where non-uniform tissue samples are provided this can require removal and manual reorientation of the tissue specimen block on the chuck in order to obtain a desired tissue section. This may result in waste of material as well.

Some known microtome chucks, if rotatable, are rotatable in one dimension only. Furthermore, if laboratory personnel desire to return the tissue chuck to an initial or previous position, it is difficult to return the tissue chuck exactly to the initial or previous position.

Another disadvantage of typical known microtome chucks is that a center of rotation for rotatable chucks is located at the chuck, which is a certain distance away from a cutting plane. This causes the tissue specimen to turn away from a cutting blade during adjustment of the tissue chuck.

Accordingly, there exists a need for a material workpiece chuck that is adjustable in multiple dimensions.

SUMMARY OF THE INVENTION

The present invention alleviates to a great extent the disadvantages of the known tissue block chucks by providing a multi-axis workpiece chuck. In accordance with the present invention, the chuck provides a mounting assembly that retains a workpiece, such as a tissue specimen block in a substantially fixed orientation with respect to the chuck.

The chuck is motor-driven and is rotatable about at least two (2) axes. The chuck is preferably rotatable using a controller that is in communication with the motor(s). A user operates the controller. The user inputs a desired position for the chuck using the controller. One or more sensors may be used to sense a particular position of the chuck. According to one embodiment, each axis has three (3) sensors that detect a middle nominal position and end positions of the chuck. The user controls movement of the chuck using the controller that commands the motor to rotate the chuck to the desired position. The controller is in communication with the sensors and determines whether a particular position has been reached. The user may cause the motor to rotate the chuck until the particular position matches the desired position.

The chuck includes first and second portions that are rotatable about at least two orthogonal axes. The first portion rotates about a first axis and independently of the second portion. Rotation of the second portion about a second axis causes the first portion to rotate about the second axis also. This enables the chuck to be rotatable in multiple dimensions.

These and other features and advantages of the present invention will be appreciated from review of the following detailed description of the invention, along with the accompanying figures in which like reference numbers refer to like parts throughout.

DETAILED DESCRIPTION OF THE INVENTION

In the following paragraphs, the present invention will be described in detail by way of example with reference to the accompanying drawings. Throughout this description, the preferred embodiments and examples shown should be considered as exemplars, rather than as limitations on the present invention. As used herein, the "present invention" refers to any one of the embodiments of the invention described herein, and any equivalents. Furthermore, reference to various aspects of the invention throughout this document does not mean that all claimed embodiments or methods must include the referenced aspects.

Figure 1:
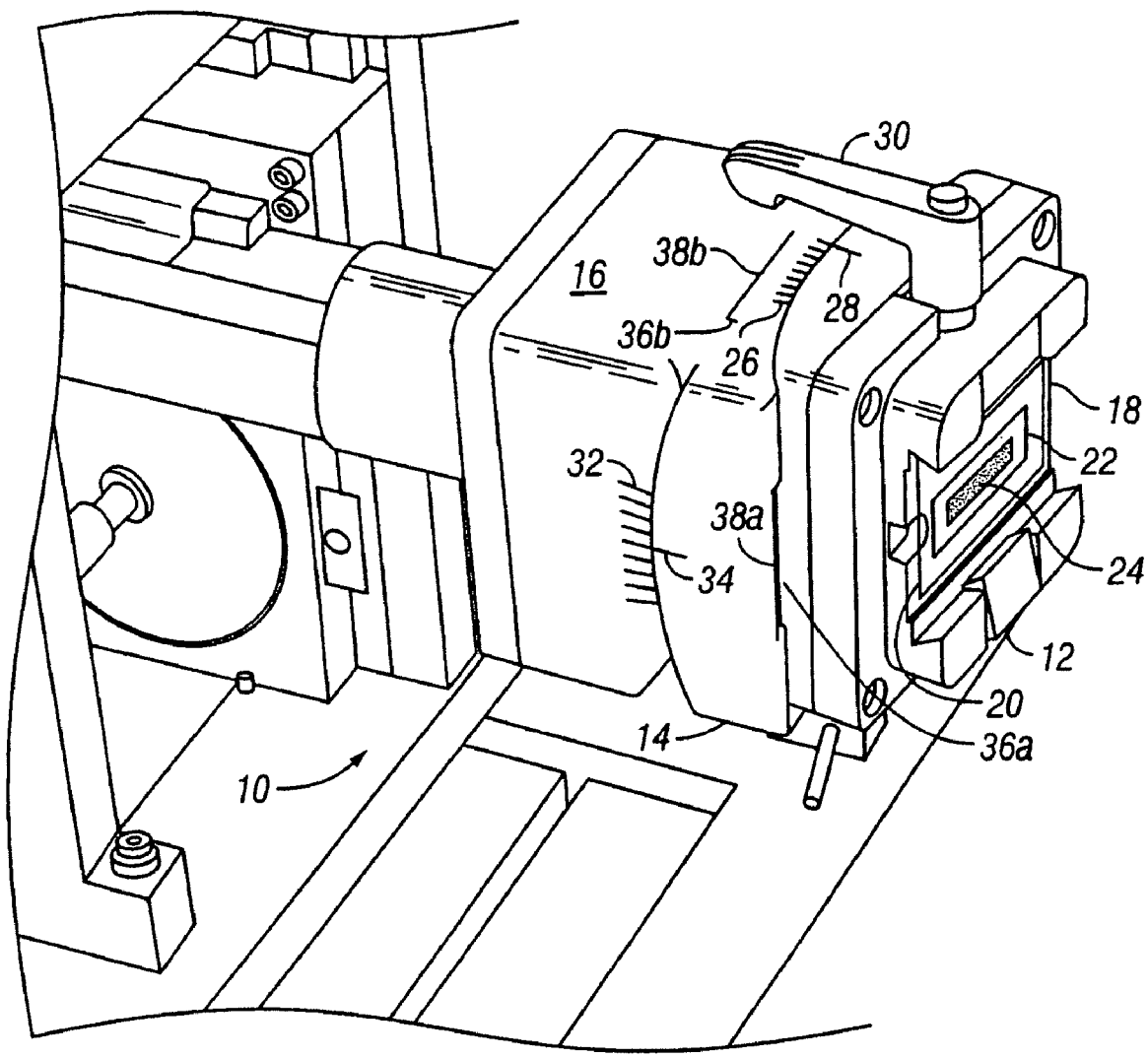
FIG. 1 is a top/side view of a multi-axis chuck according to one embodiment of the invention.

FIG. 1 illustrates a multi-axis chuck 10 according to one embodiment of the invention. The multi-axis chuck 10 includes mounting elements, namely a first portion 12, a second portion 14, and third portion 16. The front portion 12 includes a substrate receiving surface 18 and a cutting region 20.

A rear side of the first portion 12 is adjacent a front side of the second portion 14 and a rear side of the second portion 14 is adjacent a front side of the third portion 16. The substrate receiving surface 18 may be used to receive, for example, a tissue specimen. The multi-axis chuck may be used to maintain a tissue specimen on the substrate receiving surface 18 and within the cutting region 20 such that a slice of the tissue may be cut using known mechanisms for examination of the slice under a microscope. The substrate receiving surface 18 may be formed as a slot in the front portion 12. The substrate receiving surface 18 may receive a specimen holder 22.

The second portion 14 preferably includes a first degree scale 26 that indicates a number of degrees of rotation of the first portion 12 about a first axis of the cutting region 20. The first portion 12 preferably includes a first degree indicator 28. The first degree indicator 28 indicates on the first degree scale 26 the number of degrees of rotation of the first portion 12 about a first axis of the cutting region 20. According to one embodiment, the cutting region 20 consists of a point on or adjacent the cutting region 20 about which the multi-axis chuck 10 rotates.

A locking mechanism 30 may also be provided. The locking mechanism 30 may be used to lock the specimen holder 22 in the multi-axis chuck 10. After rotating the multi-axis chuck 10 using the controller (not shown), another locking mechanism may be engaged to lock the multi-axis chuck 10 in the desired position. This locking mechanism may be, for example, a permanent magnet solenoid, a geared motor or a rotating handle that causes the first, second, and third portions 12-16 to lock by friction or other known manner.

According to one embodiment, the first portion 12 rotates about a first axis of the cutting region 20 independent of the second portion 14 and the third portion 16. That is, the first portion 12 may be rotated without moving either the second portion 14 or the third portion 16. Additionally, when the second portion 14 is rotated about a second axis of the cutting region 20, this causes the first portion 12 to rotate in the same direction as the second portion 14. Preferably, the third portion 16 remains stationary.

The third portion 16 preferably includes a second degree scale 32 that indicates a number of degrees of rotation of the first portion 12 and the second portion 14 about a second axis of the cutting region 20. The second portion 14 preferably includes a second degree indicator 34. The second degree indicator 34 indicates on the second degree scale 32 a number of degrees of rotation of the first portion 12 and the second portion 14 about a second axis of the cutting region 20. Preferably, the second axis is perpendicular to the first axis.

According to one embodiment of the present invention, the first portion 12, the second portion 14, and the third portion 16 move relative to one another using protruding and recessed curved tracks 36a-36b, 38a-38b, respectively. Rear sides of the first portion 12 and the second portion 14 include protruding curved tracks 36a, 36b, respectively, that mate with recessed curved tracks 38a, 38b provided on the front sides of the second portion 14 and the third portion 16, respectively. The protruding curved track 36a is designed such that the first portion 12 may be rotated about the cutting region 20 independently of the second and third portions 14, 16.

At least a portion of the protruding curved track 36a of the first portion 12 enters the recessed curved track 38b of the second portion 14. The protruding curved track 36a moves along the recessed curved track 38b to enable the first portion 12 to be rotated about a first axis of the cutting region 20. At least a portion of the protruding curved track 36a of the second portion 14 enters the recessed curved track 38b of the third portion 16. The protruding curved track 36a moves along the recessed curved track 38b to enable the second portion 14 to be rotated about a second axis of the cutting region 20. The second portion 14 and the first portion 12, however, are operatively coupled. Therefore, when the second portion 14 is rotated, this causes the first portion 12 to be rotated also. According to one embodiment of the present invention, the second axis is substantially perpendicular to the first axis.

Figure 2:
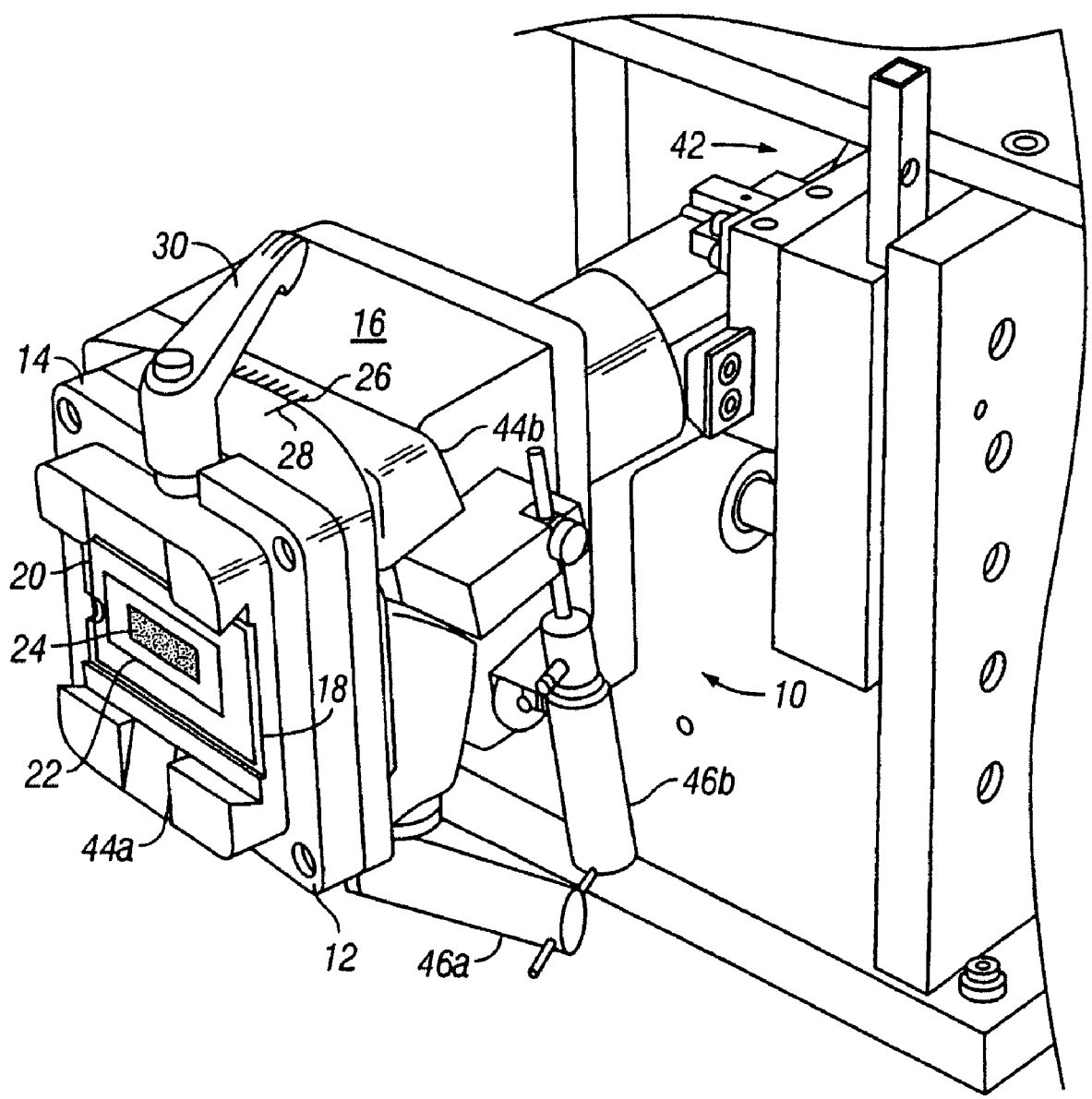
FIG. 2 is a front/side view of a multi-axis chuck according to one embodiment of the invention.

FIG. 2 is a front/side view of the multi-axis chuck 10 shown in FIG. 1. FIG. 2 illustrates a controller 42, sensors 44a, 44b, and motors 46a, 46b that may be used to rotate the multi-axis chuck 10. According to one embodiment, the sensors 44a, 44b each include three (3) separate sensors that are used to sense extreme and center positions of the multi-axis chuck 10. The motors 46a, 46b are in communication with the controller 42 and the sensors 44a, 44b. The sensors 44a, 44b are operatively connected to the motors 46a, 46b, respectively. The sensor 44a and corresponding motor 46a are operatively connected to the first portion 12. The sensor 44a is used to sense a position of the first portion 12. The motor 46a is used to rotate the first portion 12 about the first axis to a position desired by a user. The sensor 44b is used to sense a position of the first portion and the second portion 14. The motor 46b is used to rotate the first portion 12 and the second portion 14 about the second axis to a position desired by the user. According to one embodiment, the multi-axis chuck 10 includes two motors that each control rotation of the multi-axis chuck 10 about one of the first axis and the second axis. Preferably, three (3) sensors are provided along each of the first axis and the second axis for sensing the position of the multi-axis chuck 10 about the first axis and the second axis.

According to one embodiment, the controller 42 may store a zero position of the multi-axis chuck 10. The zero position may be, for example, a home or initial position in which the first portion 12 and the second portion 12 of the multi-axis chuck 10 are positioned at a most common or starting position. The starting position may be, for example, when the first portion 12 and the second portion 14 are positioned at zero degrees of rotation from the cutting region 20. The zero position may be based on a number of degrees of rotation about the first and second axes.

According to another embodiment, the controller 42 may store a plurality of positions in a memory of the controller 42 such that a user may quickly position the multi-axis chuck 10. The motor(s) may include an encoder that enables the controller 42 to identify a position of the multi-axis chuck 10 and the user to store a plurality of positions of the multi-axis chuck 10 for quickly positioning the multi-axis chuck 10 in a particular position. The user may retrieve a stored position from the controller memory using, for example, a selectable menu. For example, if a user determines that a position of two (2) degrees of rotation about the first axis of the first portion 12 and six (6) degrees of rotation about the second axis of the first portion 12 and the second portion 14 is most frequently used, the user may store this position in the controller 42.

This position may be recalled by, for example, assigning a shortcut key to the position and, possibly, assigning a name to the shortcut key. For example, if the controller 42 includes a conventional computer keyboard, an F1 function key may be assigned as the zero position where the first portion 12 and the second portion 14 are at zero degrees of rotation about the first axis and the second axis and an F2 function key may be assigned as a commonly used position shortcut key. Alternatively, a combination of keys or a numeric key input may be used. For example, a Shift-Z key combination may be used as the zero position shortcut key and an input of 12 may be used as the commonly used position shortcut key.

According to one embodiment, the controller may also store extreme positions of the multi-axis chuck. For example, the controller may store a maximum degree of rotation of the first portion about the first axis and a maximum degree of rotation of the first portion and the second portion about the second axis. These extreme positions may also be assigned as shortcut keys such that a user may quickly position the portions in these extreme positions.

A user of the multi-axis chuck 10 may use the controller 42 to position the multi-axis chuck 10 in a desired position. The desired position may be input using, for example, a joystick controller, four-way keypad or particular degrees of rotation about a predetermined axis using a keypad of a processor. The user may use the controller 42 to rotate the first portion 12 and/or the first portion 12 and the second portion 14. The user may initiate rotation of the portion(s) 12, 14 by moving a joystick such that the portion(s) 12, 14 rotate toward a desired position.

Alternatively, the user may input a number of degrees to rotate the portion(s) about the cutting region 20 using a numeric keypad in communication with the controller 42. The number of degrees of rotation may correspond to a number on the first degree scale 26, the second degree scale 32, or both. For example, the user may input into the controller 42 a three (3) degree clockwise rotation for the first portion 12 along the first degree scale 26 and a five (5) degree counterclockwise rotation for the first portion 12 and the second portion 14 along the second degree scale 32. According to one embodiment, the user may also rotate the portion(s) 12, 14 using directional keys, for example, arrow keys, on a keyboard in communication with the controller 42. The user may, for example, press and hold an arrow key until the portion(s) are in a desired position.

Figure 3:
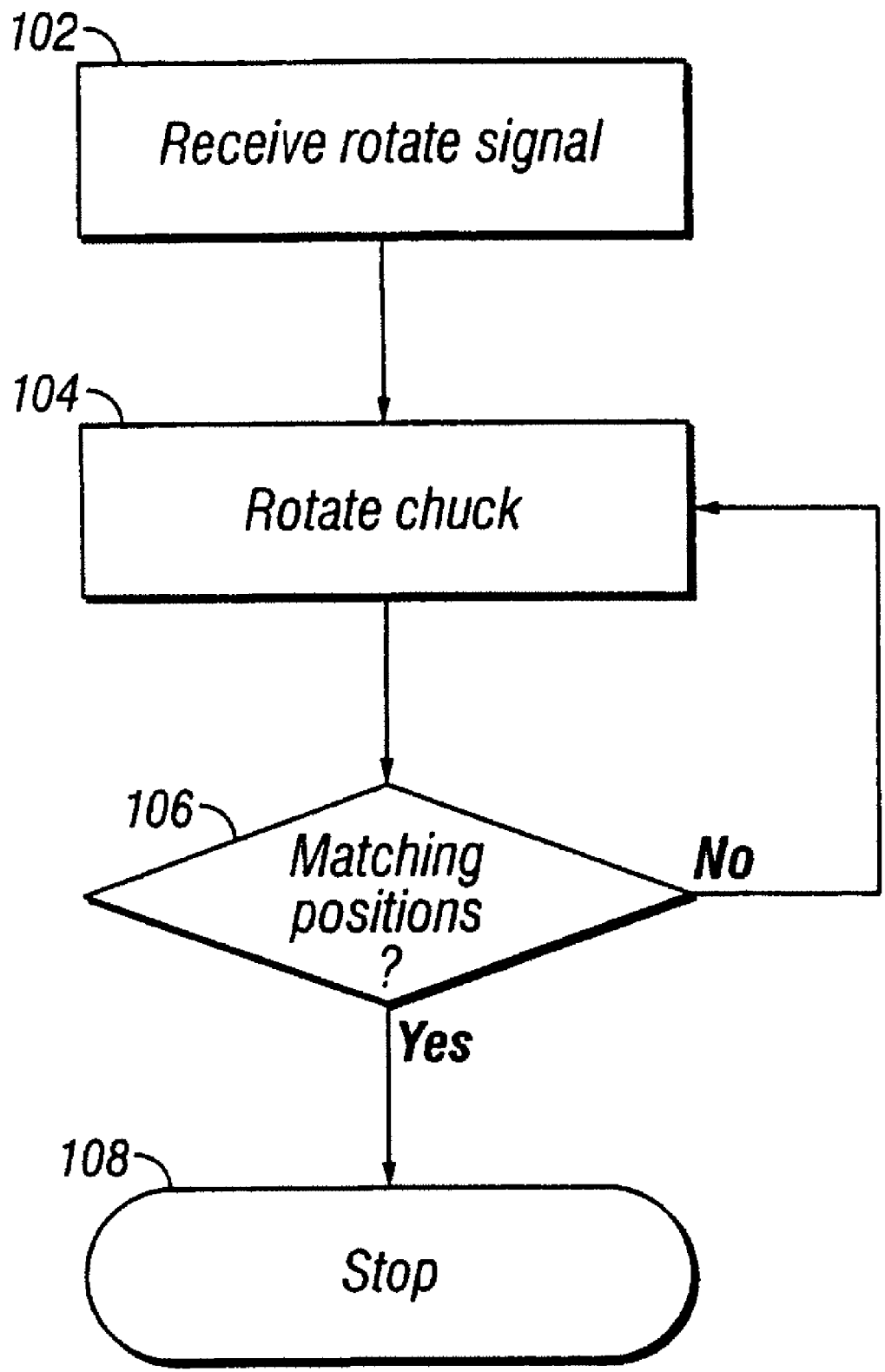
FIG. 3 is a schematic block diagram of a method for rotating a multi-axis chuck according to one embodiment of the invention.

FIG. 3 illustrates a method for rotating a multi-axis chuck according to one embodiment of the present invention. A rotate signal is received by a controller, step 102. The multi-axis chuck is rotated from a first position to a second position, step 104. The controller determines whether the second position matches a desired position input by a user using the controller, step 106. If a determination is made that the second position does not match the desired position, the multi-axis chuck may be rotated, step 104. The steps of rotating and determining may be repeated until the second position matches the desired position. After a determination is made that the second position matches the desired position, the multi-axis chuck stops rotating, step 108.

According to one embodiment, the controller may record a predetermined number of positions where the multi-axis chuck stopped. This may be used to repeat the previous positions in which the multi-axis chuck stopped. For example, if a user determines that a sequence of positions of the multi-axis chuck assists in obtaining preferred tissue specimens, the user may instruct the controller to repeat the sequence of positions. This may be done, for example, by having the controller automatically record the sequence of positions where the multi-axis chuck stops, indicating a start position and a stop position by inputting a command into the controller at the start and stop positions, etc.

Thus, it is seen that a multi-axis chuck is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

INDUSTRIAL APPLICABILITY

The multi-axis chuck of the present invention may be used in a variety of applications. For example, the multi-axis chuck may be used in combination with a bench-top microtome. The multi-axis chuck may be used to position a tissue specimen in a desired position and at a desired angle such that a microtome may be used to evenly and finely slice a portion of the tissue.

The multi-axis chuck may also be used with a cryostat. The multi-axis chuck may be located in a cryostat for positioning tissue specimens that need to be maintained in a refrigerated state of −20 degrees Celsius or below. The multi-axis chuck may be used to better position the tissue specimen for obtaining an even and finely sliced portion of the tissue specimen.

The multi-axis chuck may also enable a previously sectioned block to be re-sectioned at substantially the same angle as before. This is due to a memory location compatibility of the controller and position feedback.

What is claimed is:

1. A method comprising:
    positioning a tissue sample within a cutting region of a first portion of a chuck, wherein the chuck further comprises a second portion coupled to the first portion and the first portion is rotatable about a first axis of the cutting region and the second portion is rotatable about a second axis of the cutting region;
    rotating at least one of the first portion about the first axis and the second portion about the second axis; and
    storing a position corresponding to at least one of the first portion and the second portion in a controller memory associated with the chuck.

2. The method of claim 1, wherein rotating comprises rotating the first portion about the first axis and rotating the second portion about the second axis.

3. The method of claim 1, wherein rotating the second portion comprises rotating the first portion and the second portion about the second axis.

4. The method of claim 1, wherein rotating comprises instructing a controller to rotate the at least one of the first portion and the second portion.

5. The method of claim 1, wherein instructing comprises providing the controller with a number of degrees of rotation.

6. The method of claim 1, further comprising:
    storing a plurality of positions into the controller memory associated with the chuck, each of the plurality of positions comprising a degree of rotation about at least one of the first axis and the second axis,
    wherein rotating comprises rotating the at least one of the first portion and the second portion to at least one of the plurality of positions.

7. A method of zeroing a multi-axis chuck comprising:
    receiving a signal to rotate a multi-axis chuck to a first position stored in a memory of a controller associated with the multi-axis chuck;
    rotating the multi-axis chuck to a second position;
    comparing the second position to the first position; and
    repositioning the multi-axis chuck if a determination is made that the second position is not at the first position.

8. The method of claim 7, wherein rotating comprises rotating by at least one motor.

9. The method of claim 8, further comprising controlling the at least one motor by a controller.

10. The method of claim 9, wherein comparing comprises sensing with at least one sensor in communication with the controller.

* * * * *